(12) United States Patent
Sugiura et al.

(10) Patent No.: US 6,209,540 B1
(45) Date of Patent: Apr. 3, 2001

(54) ARTIFICIAL RESPIRATION APPARATUS

(75) Inventors: Yasuhito Sugiura; Mikio Yasukawa; Katsuyoshi Suzuki; Masahiro Kamada; Toshihisa Takaki, all of Shizuoka; Kazufuku Nitta, Saitama; Yoshitsugu Yamada, Tokyo, all of (JP)

(73) Assignee: Suzuki Corporation, Shizouka (JP)

( * ) Notice: Subject to any disclaimer, the term of this patent is extended or adjusted under 35 U.S.C. 154(b) by 0 days.

(21) Appl. No.: 09/280,973

(22) Filed: Mar. 30, 1999

(30) Foreign Application Priority Data

Mar. 31, 1998 (JP) .................................................. 10-103741

(51) Int. Cl.[7] .................................................. A61M 16/00
(52) U.S. Cl. .............................. 128/204.18; 128/204.21; 128/204.24; 128/205.24; 601/41
(58) Field of Search ...................... 128/204.18, 204.21, 128/204.23, 204.24, 205.24; 601/41, 48; 600/523

(56) References Cited

U.S. PATENT DOCUMENTS

| | | | |
|---|---|---|---|
| 4,397,306 | * 8/1983 | Weisfeldt et al. | 601/43 |
| 4,770,165 | * 9/1988 | Hayek | 128/205.18 |
| 5,526,805 | * 6/1996 | Lutz et al. | 128/204.18 |
| 5,850,835 | * 12/1998 | Takaki et al. | 128/204.18 |
| 5,988,166 | * 11/1999 | Hayek | 128/205.26 |

* cited by examiner

Primary Examiner—John G. Weiss
Assistant Examiner—V. Srivastava
(74) Attorney, Agent, or Firm—Greenblum & Bernstein, P.L.C.

(57) ABSTRACT

The present invention provides a small-size, small-weight, low-cost artificial respiration apparatus which can easily be used in an ordinary hospital.

The artificial respiration apparatus 10 includes: a positive blower 12p for generating a positive air pressure Ap; a negative blower 12n for generating a negative air pressure An; a rotary valve mechanism 54 for alternately selecting the positive pressure Ap generated by the positive blower 12p and the negative pressure An generated by the negative blower 12n and converting them into an oscillating air pressure Apn; and a diaphragm block 56 urged by the oscillating air pressure Apn from the rotary valve mechanism 54 to operate to supply air to a patient P. Use of the positive blower 12p and the negative blower 12n significantly reduces the load, enabling to use ones available on market, i.e., small-size, small-weight, low-consumption blowers.

7 Claims, 5 Drawing Sheets

ARTIFICIAL RESPIRATION APPARATUS

BACKGROUND OF THE INVENTION

1. Field of the Invention

The present invention relates to an artificial respiration apparatus that forcibly supplies air to a patient who cannot breathe by himself/herself and that can operate so as to reduce the load on the patient when the patient spontaneously starts breathing.

2. Description of the Related Art

FIG. 5 shows a configuration of a conventional artificial respiration apparatus. Hereinafter, explanation will be given on the conventional artificial respiration apparatus with reference to FIG. 5.

The conventional respiration apparatus 50 includes: a blower 52 for simultaneously generating a positive pressure Ap and a negative pressure An; a rotary valve mechanism 54 for alternately selecting the positive pressure Ap and the negative pressure An generated by the blower 52 and converting the positive and negative pressures into an oscillating air pressure Apn; and a diaphragm block 56 which is urged by the oscillating air pressure Apn from the rotary valve mechanism 54, so as to supply air to a patient P. Moreover, the artificial respiration apparatus 50 includes: a diaphragm neutral position controller 60 for maintaining a neutral position of a diaphragm 561 of the diaphragm block 56; and a respiration gas port 62 for introducing the respiration gas.

The blower 52 has a positive pressure pipe 521 and a negative pressure pipe 522, so that air is supplied to the blower 52 through the negative pressure pipe 522 and discharges the air through the positive pressure pipe 521. The negative pressure pipe 522 is connected to an orifice pipe 523 communicating with the open air. The positive pressure pipe 521 is connected to an orifice pipe 524 communicating with the open air.

The rotary valve mechanism 54 is constituted by a rotary valve 544 having ports 541, 542, 543, and a drive block 545 for rotating the rotary valve 544. The drive block 545 includes a motor and a reduction gear (not depicted) so as to rotate the rotary valve 544 at 900 rpm for example. While the rotary valve 544 makes a single turn, the port 541 and the port 542 are successively made to communicate with the port 543. The port 543 is connected to an oscillating air pressure pipe 546 for transmitting the oscillating air pressure Apn to the diaphragm block 56. A flow control valve 547 is inserted into the oscillating air pressure pipe 546.

The diaphragm block 56 includes a diaphragm 561 formed by an expandable member serving as a partition between a pressurizing chamber 562 and a pressurized chamber 563. The pressurizing chamber 562 is connected to the oscillating air pressure pipe 546.

The respiration gas port 62 is constituted by a blender 621 for mixing the open air with oxygen prepared in advance; and a humidifier 622 for humidifying the gas to be sent out from the blender 521. The humidifier 622 is connected to a respiration gas pipe 623 for supplying to the patient P the respiration gas Ai which has passed through the humidifier. The respiration gas pipe 623 communicates with the pressurized chamber 563 and has a pressure sensor 624 provided in the vicinity of the patient P.

The diaphragm neutral position controller 60 includes: a diaphragm position sensor 601 for detecting a position of the diaphragm 561 of the diaphragm block 56; a pressure regulating valve 64 for controlling the positive pressure Ap, the negative pressure An, or the oscillating air pressure Apn; a control block 66 for controlling the pressure regulating valve 64 according to the position of the diaphragm 561 detected by the diaphragm position sensor 601.

The pressure regulating valve 64 has a configuration similar to a rotary valve and is constituted by a main body 646 having ports 641 to 645 and an actuator 647 for rotating a part of the main body in normal and reverse directions. The actuator 647 is constituted by a motor and a reduction gear (not depicted) and can rotate a part of the main body 646 by a desired angle. The control block 66 is, for example, a microcomputer including a CPU, ROM, RAM, I/O interface, and the like.

In the artificial respiration apparatus 50, the single blower 52 serves to generate both of the positive pressure and the negative pressure. That is, the blower 52 has a large load. On the other hand, in order to increase the ventilation amount of the artificial respiration apparatus 50, it is most effective to increase the power of the blower 52. However, if the power is to be increased with the single blower 52, it becomes necessary to design a special blower having very large dimensions and weight. Such a blower is not available on market and should be prepared by a special order.

This has been preventing reduction in size and weight as well as cost of the conventional artificial respiration apparatus 50. Moreover, such a large blower 52 requires a 200 V power source or a large current receptacle even if a 100 V power source can be used. This makes it difficult to use the artificial respiration apparatus 50 even in a small hospital.

Next, explanation will be given on the reason why the blower 52 of the artificial respiration apparatus 50 should have such a large load. A "blower" is an apparatus constituted by a motor and a fan for sucking air from the suction side and discharging the air from the discharge side. The blower 52 generates a negative pressure An by sucking air from the suction side and generates a positive pressure Ap by discharging the sucked air from the discharge side.

Here, for use of the positive pressure Ap, the rotary valve mechanism 54 makes the discharge side of the blower 52 communicate with the oscillating air pressure pipe 546 while closing the suction side of the blower 52. Here, if the suction side is closed completely, it becomes impossible to obtain air for discharge. Accordingly, the suction side is connected to the orifice pipe 523 communicating with the open air.

On the contrary, when using the negative pressure An, the rotary valve mechanism 54 makes the discharge side of the blower 52 closed and the suction side of the blower 52 communicate with the oscillating air pressure pipe 546. Here, if the discharge side is closed completely, the sucked air cannot be discharged. Accordingly, the discharge side is also connected to an orifice pipe 524 communicating with the open air.

Accordingly, when using the positive air Ap, the suction side takes in air via the orifice pipe 523, whereas the discharge side discharges the air via the oscillating air pressure pipe 546 and simultaneously with this, the air leaks out via the orifice pipe 524. On the contrary, when using the negative pressure An, the discharge side discharges air via the orifice pipe 524, whereas the suction side sucks air via the oscillating air pressure pipe 546 and simultaneously with this, air flows in via the orifice pipe 523. Thus, operation of the artificial respiration apparatus 50 is inevitably accompanied by useless air leak out and flow in. This significantly increases the load of the blower 52.

SUMMARY OF THE INVENTION

It is therefore an object of the present invention to provide an artificial respiration apparatus which can realize a small size, small weight, and low production cost and can be used in small hospitals.

The inventors of the present invention have found that the aforementioned object can be achieved by replacing the blower generating both of a positive pressure and a negative pressure by a positive pressure blower for generating only a positive pressure in combination with a negative pressure blower for generating only a negative pressure. This can significantly reduce the load (i.e., power consumption), which in turn realizes a smaller size and weight as well as a lower cost. For example, instead of a large-size blower of a special type, ordinary two blowers are used. Such an ordinary blower is small in size and weight and is available on market, and can be used with a 100V commercial power source.

The present invention is based on this finding. That is, the artificial respiration apparatus according to the present invention comprises: a positive pressure generator for generating a positive air pressure; a negative pressure generator for generating a negative air pressure; an oscillating air pressure generation mechanism for alternately selecting the positive pressure generated by the positive pressure generator and the negative pressure generated by the negative pressure generator so as to convert the positive pressure and the negative pressure into an oscillating air pressure; and a diaphragm block urged by the oscillating air pressure from the oscillating air pressure generation mechanism, so as to supply a gas into a mouth of a patient.

Next, explanation will be given on the reason why the load is reduced when the one blower is replaced by two blowers.

The artificial respiration apparatus according to the present invention includes: a negative pressure blower (negative pressure generator) which sucks air at its suction side and discharging the sucked air into the open air, thus generating a negative pressure; and a positive pressure blower (positive pressure generator) which sucks air from the open air and discharges the sucked air to its discharge side, thus generating a positive pressure.

Here, when using the positive pressure, a rotary valve mechanism (oscillating air pressure generation mechanism) makes the discharge side of the positive pressure blower communicate with an oscillating air pressure pipe and the suction side of the negative blower closed. Here, even if the suction side of the negative pressure blower is closed completely, the positive pressure blower can suck air from the open air. Accordingly, the orifice pipe used at the suction side in the conventional respirator is not required.

On the contrary, when using the negative pressure, the rotary valve mechanism (oscillating air pressure generation mechanism) makes the discharge side of the positive pressure blower closed and the suction side of the negative pressure blower communicate with the oscillating air pressure pipe. Here, even if the suction side of the positive pressure blower is closed completely, the negative pressure blower can discharge air into the open air. Accordingly, the orifice pipe used at the discharge side in the conventional respirator is not required.

Consequently, in the artificial respiration apparatus according to the present invention, there is no useless air leak out or flow in. This can significantly reduce the blower load. For example, the conventional respirator requires a single blower of 1.35 KW, whereas the present invention requires only 0.85 KW for use of two blowers in combination. Thus, the power consumption is reduced by about 37%.

DESCRIPTION OF THE PREFERRED EMBODIMENTS

Figure 1:
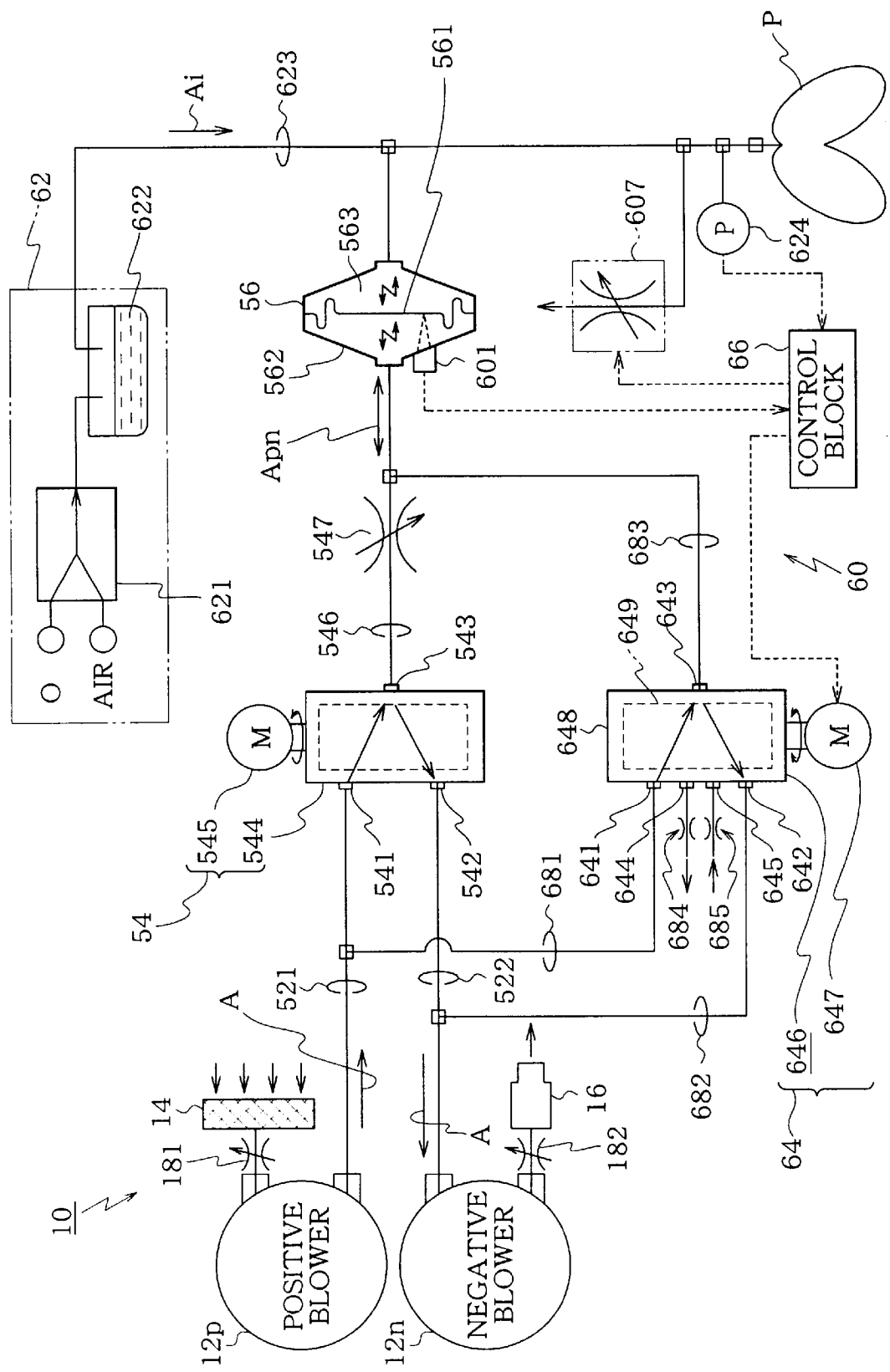
FIG. 1 shows a configuration of an artificial respiration apparatus according to an embodiment of the present invention.
Figure 2:
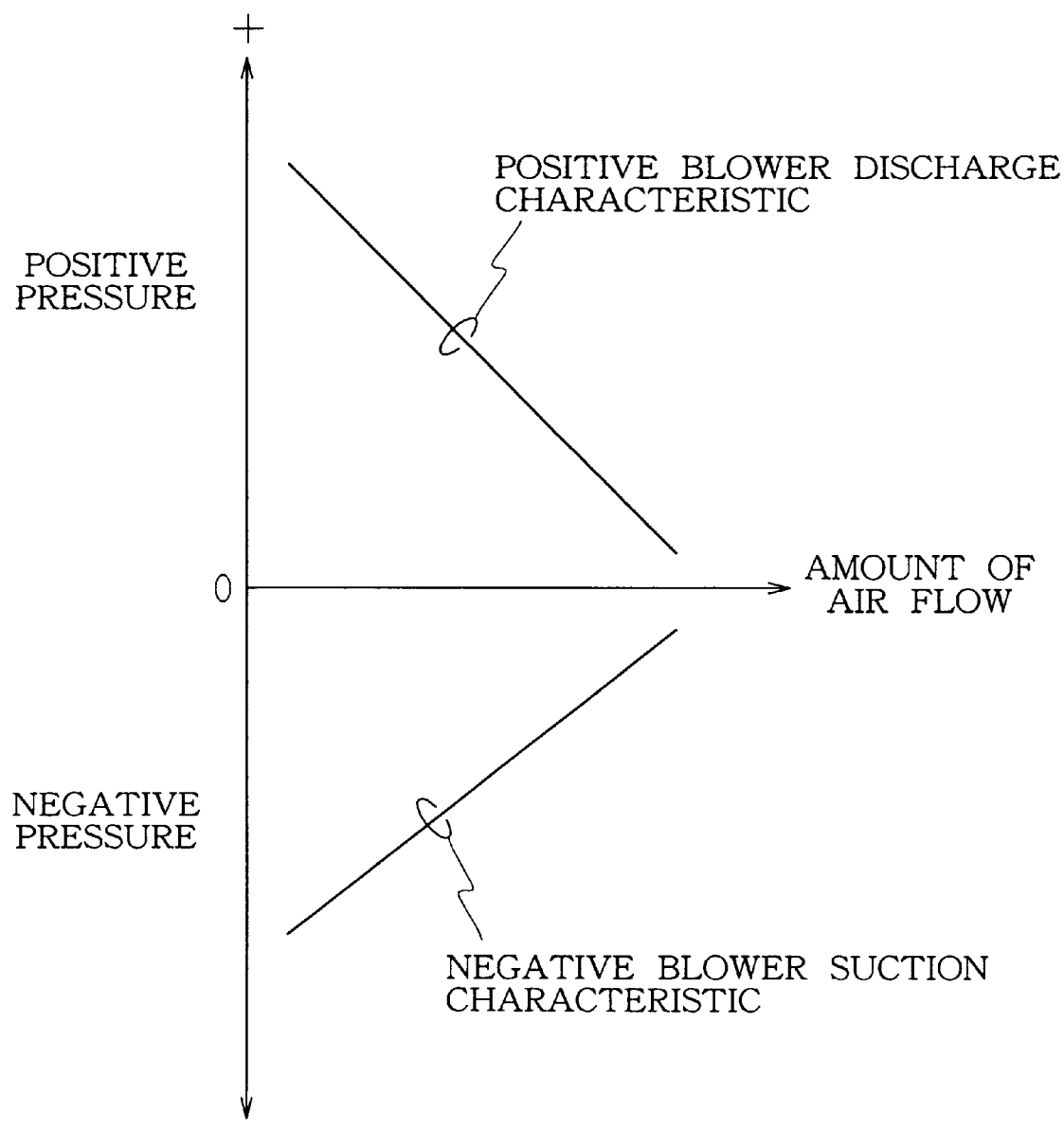
FIG. 2 is a graph showing as an example, discharge characteristic of a positive pressure blower and suction characteristic of a negative pressure blower in the artificial respiration apparatus shown in FIG. 1.
Figure 5:
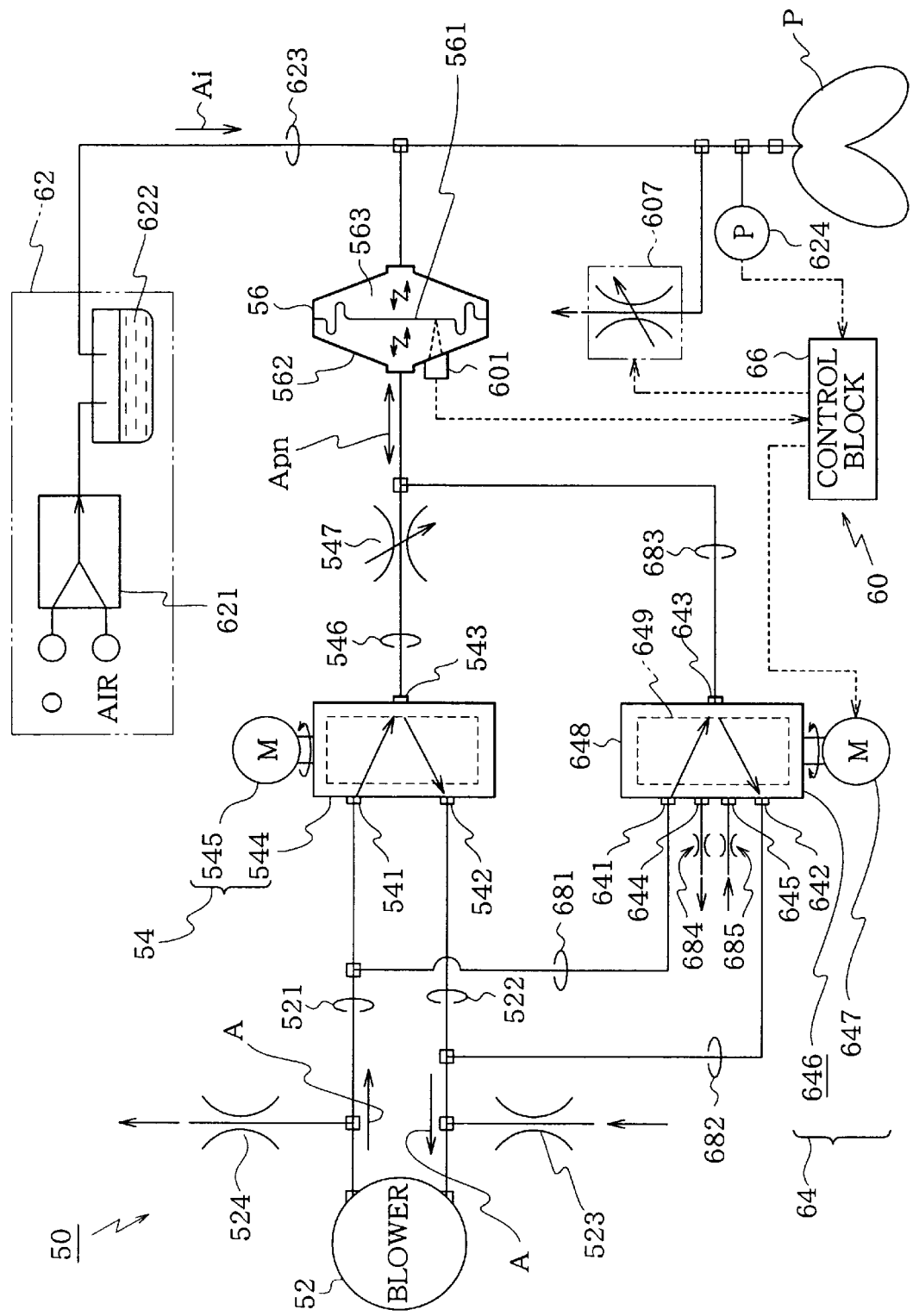
FIG. 5 shows a configuration of a conventional artificial respiration apparatus.

FIG. 1 shows a configuration of an artificial respiration apparatus according to an embodiment of the present invention. FIG. 2 is a graph showing as an example, discharge characteristic of a positive pressure blower and suction characteristic of a negative pressure blower in the artificial respiration apparatus shown in FIG. 1. Hereinafter, explanation will be given with reference to FIG. 1 and FIG. 2. It should be noted that like components as in FIG. 5 are denoted by like reference symbols without giving any detailed explanation.

The artificial respiration apparatus 10 according to the present embodiment includes: a positive blower 12p (positive pressure generator) for generating a positive pressure Ap; a negative blower 12n (negative pressure generator) for generating a negative pressure An; a rotary valve mechanism 54 (oscillating air pressure generation mechanism) alternately selecting the positive pressure Ap generated by the positive blower 12p and the negative pressure An generated by the negative blower 12n; and a diaphragm block 56 urged by the oscillating air pressure Apn from the rotary valve mechanism 54 so as to supply air to the patient P.

The positive blower 12p sucks air via a filter 14 from the atmosphere and discharges the sucked air to a positive pressure pipe 521 to generate a positive pressure Ap. The filter 14 serves to remove dusts from the air to be sucked. The negative blower 12n sucks air from the negative pressure pipe 522 and discharges the sucked air via a silencer 16 into the atmosphere, thus generating the negative pressure An. The silencer 16 serves to reduce the sound caused by air discharge. Moreover, flow control valves 181 and 182 are provided at the suction side of the positive blower 12p and the discharge side of the negative blower 12n, respectively.

Moreover, as shown in FIG. 2, the discharge characteristic of the positive blower 12p is symmetric to the suction characteristic of the negative blower 12n. Accordingly, the absolute value of the positive pressure Ap is almost equal to the absolute value of the negative pressure An. Deviation of the diaphragm 561 (deviation from an average neutral position), as will be detailed later, is dissolved by a diaphragm neutral position controller 60. As the difference between the absolute value of the positive pressure Ap and the that of the negative pressure An increases, the deviation of the diaphragm 561 becomes difficult to be dissolved by the diaphragm neutral position controller 60. Accordingly, it is preferable that the discharge characteristic of the positive blower 12p be symmetric to the suction characteristic of the negative blower 12n.

It should be noted that even if the positive blower 12p has a discharge characteristic not symmetric to the suction characteristic of the negative blower 12n, it is possible to make adjustment within a certain range using the diaphragm neutral position controller 60 or the flow control valves 181, 182.

Figure 3:
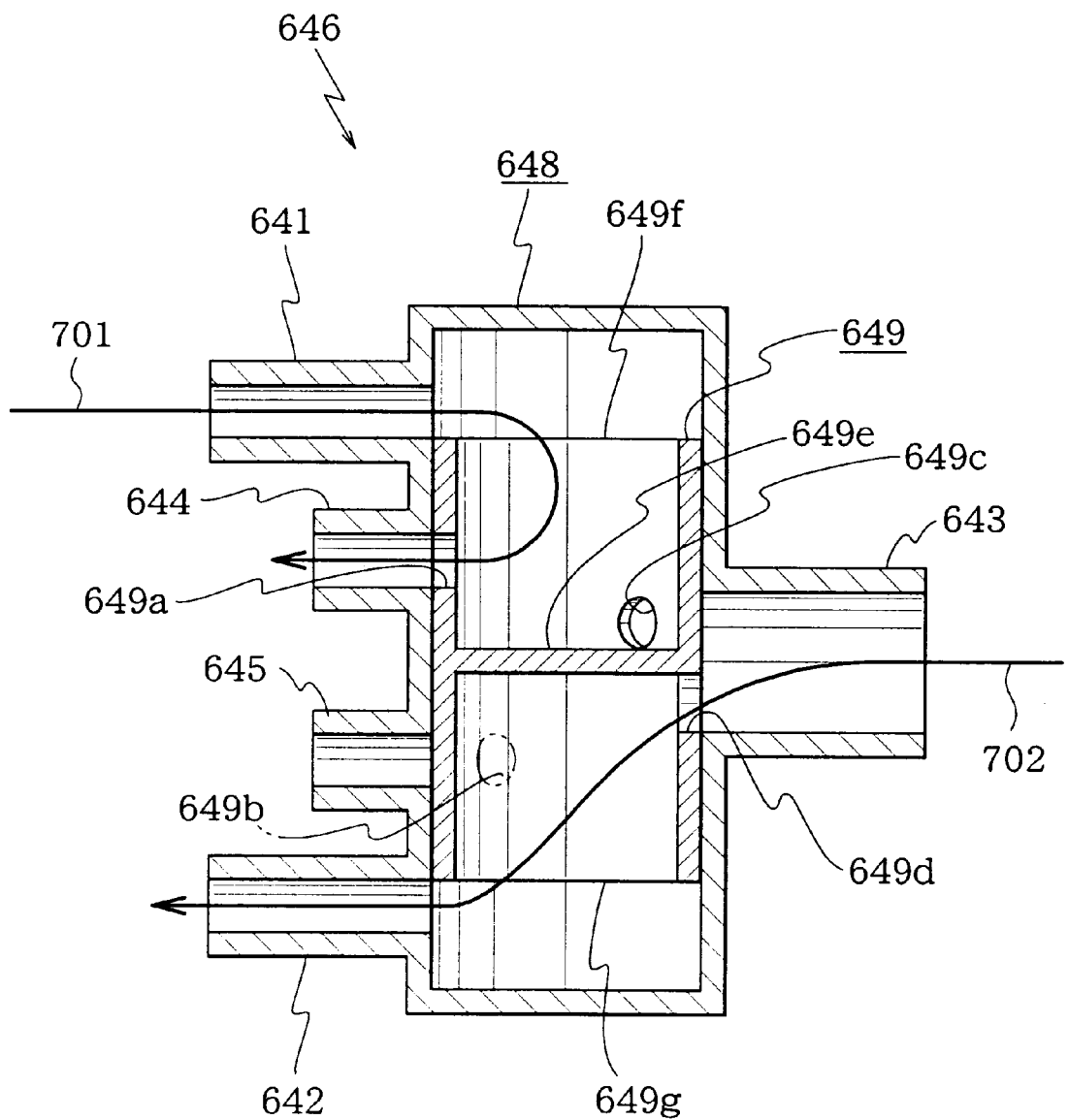
FIG. 3 is a cross sectional view of a pressure regulating valve used in a diaphragm neutral position controller of FIG. 1 in a state for selecting a positive pressure releasing passage and a negative pressure application passage.
Figure 4:
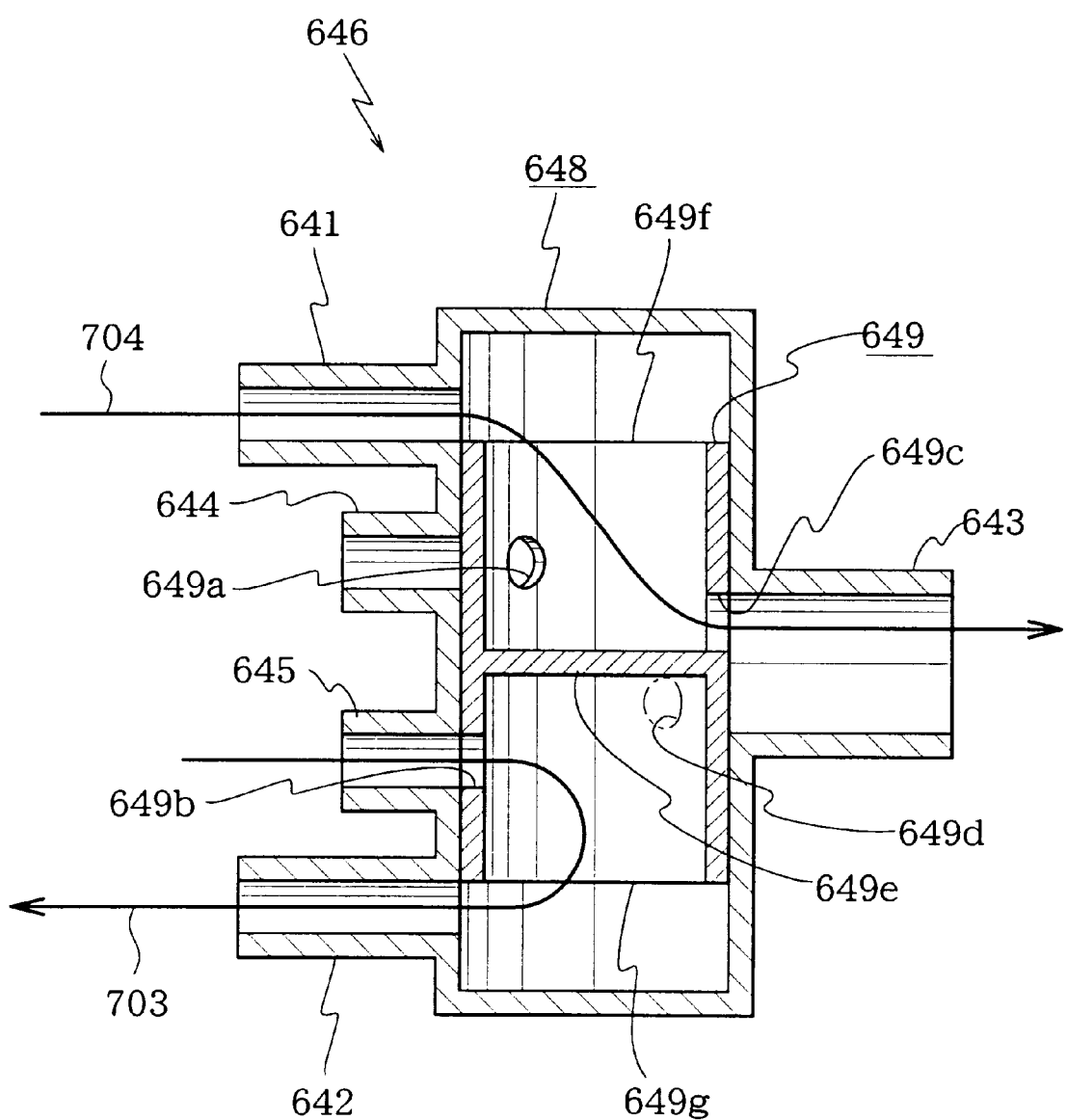
FIG. 4 is a cross sectional view of the pressure regulating valve used in the diaphragm neutral position controller of FIG. 1 in a state for selecting a negative pressure releasing passage and a positive pressure application passage.

FIG. 3 and FIG. 4 are cross sectional views of a main body 646 of the pressure regulating valve 64 as an example. Hereinafter, explanation will be given with reference to FIG. 1 to FIG. 4.

The main body 646 of the pressure regulating valve 64 is constituted by a fixed body 648 as an outer cylindrical member and a rotary body 649 as an inner cylindrical shape. The fixed body 648 has ports 641 to 645. The rotary body 649 has through holes 649a, 649b, 649c, 749d, a partition 649e, and opening ends 649f, 649g.

The port 641 is connected to a positive pressure bypass pipe 681 which communicates with the positive pressure pipe 521. The port 642 is connected to a negative pressure bypass pipe 682 which communicates with the negative pressure pipe 522. The port 643 is connected to an oscillating air pressure bypass pipe 683 which communicates with the oscillating air pressure pipe 546. The ports 644 and 645 are connected to open air ports 684 and 685, respectively.

The rotary body 649 is rotated by an actuator 647. The rotary body 649, according to its rotation angle, can select a positive pressure releasing passage 701 in combination with a negative pressure application passage 702 (FIG. 3); or a negative pressure releasing passage 703 in combination with a positive pressure application passage 704 (FIG. 4).

The positive pressure releasing passage 701 allows the air to flow through the positive bypass pipe 681, the port 641, the opening end 649f, the through hole 649a, the port 644, and the orifice pipe 684 in this order. This passages lowers the absolute value of the positive pressure Ap generated by the positive blower 12p.

The negative pressure application passage 702 allows the air to flow through the oscillating air pressure bypass pipe 683, the port 643, the through hole 649d, the opening end 649g, the port 642, and the negative pressure bypass pipe 682 in this order. This passage applies the negative pressure An generated by the negative blower 12n, to the oscillating air pressure Apn urging the diaphragm 561.

The negative pressure releasing passage 703 allows the air to flow through the orifice pipe 685, the port 645, the opening end 649g, the port 642, and the negative pressure bypass pipe 682 in this order. This passage lowers the absolute value of the negative pressure generated by the negative blower 12n.

The positive pressure application passage 704 allows the air to flow through the positive bypass pipe 681, the port 641, the opening end 649f, the through hole 649c, the port 643, and the oscillating air pressure bypass pipe 683 in this order. This passage applies the positive pressure Ap generated by the positive blower 12p, to the oscillating air pressure Apn urging the diaphragm 561.

The amount of the air flowing through the respective passages can be continuously changed by rotating in jog mode the rotary body 649 using the actuator 647. Moreover, the rotary body 649 can also be set at an angle not selecting any of the passages.

Description will now be directed to operation of the artificial respiration apparatus 10.

The positive pressure Ap generated by the positive blower 12p and the negative pressure generated by the negative blower 12n are converted into an oscillating air pressure Apn by the rotary valve mechanism 54. The oscillating air pressure Apn generated by the rotary valve mechanism 54 is fed to the diaphragm block 56. In the diaphragm block 56, the diaphragm 561 is oscillated by the cycle of the oscillating air pressure Apn, and the oscillation of the diaphragm 561 changes the pressure inside the respiration gas pipe 623. Moreover, the respiration gas Ai is constantly supplied to the patient P. The exhaling air from the patient P is discharged via the flow control valve 607. The flow control valve 607 in normal mode is open to a degree that the exhaling air can flow out.

The movement of the diaphragm 561 is detected by a diaphragm position sensor 601, and the detected information is constantly fed as an operation information of the diaphragm 561 to the control block 66. If this movement of the diaphragm 561 is disturbed by a spontaneous breathing of the patient, this information is immediately fed to the control block 66, so that the control block 66 controls the flow control valve 607 to adjust the pressure inside the respiration gas pipe 623, thus reducing the load on the patient P upon his/her spontaneous breathing.

If the diaphragm neutral position is deviated from the center, the reciprocal movement of the diaphragm 561 is limited to a certain degree, making incomplete the respiration operation of the artificial respiration apparatus 10. To cope with this, the diaphragm neutral position controller 60 operates to decrease the pressure difference between the pressurizing chamber 562 and the pressurized chamber 563 within a range not disturbing operation of the diaphragm block 56, so that the diaphragm 561 can maintain its neutral position.

That is, the control block 66 constantly detects deviation from an average neutral position of the diaphragm 561 according to an operation information of the diaphragm 561 obtained from the diaphragm position sensor 601. If the average neutral position of the diaphragm 561 is deviated, the control block 66 operates as follows.

When the neutral position of the diaphragm 561 deflects toward the side of the patient P (rightward in FIG. 1), the pressure regulating valve 64 is controlled to select the positive pressure releasing passage 701 and the negative pressure application passage 702. The positive pressure releasing passage 701 decreases the absolute value of the positive pressure Ap generated by the positive blower 12p. Simultaneously with this, the negative pressure application passage 702 applies the negative pressure An generated in the negative blower 12n, to the oscillating air pressure Apn, thus lowering the oscillating air pressure Apn. This returns the neutral position of the diaphragm 561 to its center position (leftward in FIG. 1).

On the contrary, when the neutral position of the diaphragm 561 deflects toward the positive blower 12p and the negative blower 12n (leftward in FIG. 1), the pressure regulating valve 64 is controlled to select the negative pressure releasing passage 703 and the positive pressure application passage 704. The negative pressure releasing passage 703 decreases the absolute value of the negative pressure Ap generated by the negative blower 12n. Simultaneously with this, the positive pressure application passage 704 applies the positive pressure Ap generated in the positive blower 12p, to the oscillating air pressure Apn, thus increasing the oscillating air pressure Apn. This returns the neutral position of the diaphragm 561 to its center position (rightward in FIG. 1).

The time required for returning the diaphragm 561 to its center position is significantly reduced by controlling not only the positive pressure Ap but also the negative pressure An. Besides, the oscillating air pressure Apn is discharged not into the atmosphere but into the negative pressure An side or the positive pressure Ap side, so as to utilize a greater pressure difference. Thus, the time is further reduced.

It should be noted that the present invention is not to be limited to the aforementioned embodiment. For example, the rotary body 149 may be constructed so as to select one of the positive pressure releasing passage 201 and the negative pressure lowering passage 203, or one of the negative pressure application passage 202 and the positive pressure application passage 204.

The artificial respiration apparatus according to the present invention uses a positive pressure generator generating only a positive pressure in combination with a negative pressure generator generating only a negative pressure instead of using an air pressure generator generating both of a positive pressure and a negative pressure. This brings about following effects.

(1) In comparison to the conventional air pressure generator, the load of the positive pressure generator and the negative pressure generator can significantly be reduced, which in turn enables to reduce the apparatus size and weight as well as the production cost.

(2) Each of the positive pressure generator and the negative pressure generator can be realized by a small-size and small-weight blower or the like requiring a low power consumption, available on market.

(3) The positive pressure generator and the negative pressure generator are small and light. Accodingly, it is possible to provide an artificial respiration apparatus having practical dimensions and weight which can easily be handled by doctors and nurses.

(4) The positive pressure generator and the negative pressure generator consume a low power and accordingly, there is no need of preparing a special power source to use the artificial respiration apparatus in a small hospital.

(5) The positive pressure generator and the negative pressure generator are available on market without requiring a special order, and it is possible to use the artificial respiration apparatus at a low cost.

(6) The positive pressure generator and the negative pressure generator are independent components from each other. This facilitates maintenance operation.

According to another aspect of the present invention, the positive pressure generator has a discharge characteristic symmetric to a suction characteristic of the negative pressure generator. This enables to realize an ideal respiration without deviation of the neutral position of the diaphragm.

According to still another aspect of the present invention, each of the positive pressure generator and the negative pressure generator has at its discharge side a flow control valve. Accordingly, even if the discharge characteristic of the positive pressure generator is not symmetric to the suction characteristic of the negative pressure generator, it is possible to realize an ideal respiration having no deviation in the neutral position of the diaphragm.

According to yet another aspect of the present invention, a diaphragm neutral position controller is provided for maintaining the neutral position of the diaphragm. Accordingly, even if the discharge characteristic of the positive pressure generator is not symmetric to the suction characteristic of the negative pressure generator, it is possible to realize an ideal respiration having no deviation in the neutral position of the diaphragm.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 10-103741 (Filed on Mar. 31, 1998) including specification, claims, drawings and summary are incorporated herein by reference in its entirety.

What is claimed is:

1. An artificial respiration apparatus comprising:
 a positive pressure generator that generates a positive air pressure;
 a negative pressure generator that generates a negative air pressure;
 an oscillating air pressure generation mechanism that alternately selects the positive pressure generated by said positive pressure generator and the negative pressure generated by said negative pressure generator so as to convert the positive pressure and the negative pressure into an oscillating air pressure; and
 a diaphragm block urged by the oscillating air pressure from said oscillating air pressure generation mechanism and supplying air into a mouth of a patient.

2. An artificial respiration apparatus as claimed in claim 1, wherein said positive pressure generator has a discharge characteristic symmetric to a suction characteristic of said negative pressure generator.

3. An artificial respiration apparatus as claimed in claim 1, wherein a flow control valve is provided at a suction side of said positive pressure generator and at a discharge side of said negative pressure generator.

4. An artificial respiration apparatus as claimed in claim 1, said apparatus further comprising a diaphragm neutral position controller that maintains a neutral position of a diaphragm of said diaphragm block.

5. An artificial respiration apparatus as claimed in claim 3, said apparatus further comprising a diaphragm neutral position controller that maintains a neutral position of a diaphragm of said diaphragm block.

6. An artificial respiration apparatus as claimed in claim 4, wherein said diaphragm neutral position controller includes:
 a diaphragm position sensor that detects a position of said diaphragm;
 a pressure control mechanism that controls at least one of said positive pressure, said negative pressure, and said oscillating air pressure; and
 a control block that controls said pressure control mechanism according to the position of said diaphragm detected by said diaphragm position sensor.

7. An artificial respiration apparatus as claimed in claim 5, wherein said diaphragm neutral position controller includes:
 a diaphragm position sensor that detects a position of said diaphragm;
 a pressure control mechanism that controls at least one of said positive pressure, said negative pressure, and said oscillating air pressure; and
 a control block that controls said pressure control mechanism according to the position of said diaphragm detected by said diaphragm position sensor.

* * * * *

UNITED STATES PATENT AND TRADEMARK OFFICE
CERTIFICATE OF CORRECTION

PATENT NO.    : 6,209,540 B1  
DATED         : April 3, 2001  
INVENTOR(S)   : Yasuhito Sugiura et al.

It is certified that error appears in the above-identified patent and that said Letters Patent is hereby corrected as shown below:

<u>Title page</u>,
Item [73], Assignee, "Suzuki Corporation, Shizouka (JP)" should be
-- Suzuki Motor Corporation, Shizuoka, (JP)
Yoshitsugu Yamada, Tokyo (JP)
Japan Science and Technology Corporation, Saitama (JP) --

Signed and Sealed this

Second Day of July, 2002

*Attest:*

JAMES E. ROGAN
*Attesting Officer*    *Director of the United States Patent and Trademark Office*